US012758165B2

(12) United States Patent
Stopp et al.

(10) Patent No.: US 12,758,165 B2
(45) Date of Patent: Oct. 13, 2026

(54) MOIRÉ MARKER FOR X-RAY IMAGING

(71) Applicant: Brainlab AG, Munich (DE)

(72) Inventors: Sebastian Stopp, Munich (DE); Nils Frielinghaus, Munich (DE)

(73) Assignee: Brainlab SE, Munich (DE)

( * ) Notice: Subject to any disclaimer, the term of this patent is extended or adjusted under 35 U.S.C. 154(b) by 224 days.

(21) Appl. No.: 17/927,063

(22) PCT Filed: May 29, 2020

(86) PCT No.: PCT/EP2020/065040
§ 371 (c)(1),
(2) Date: Nov. 22, 2022

(87) PCT Pub. No.: WO2021/239256
PCT Pub. Date: Dec. 2, 2021

(65) Prior Publication Data
US 2023/0210478 A1 Jul. 6, 2023

(51) Int. Cl.
*A61B 6/04* (2006.01)
*A61B 6/00* (2024.01)

(52) U.S. Cl.
CPC .............. *A61B 6/0492* (2013.01); *A61B 6/52* (2013.01); *A61B 6/5294* (2013.01); *A61B 6/5211* (2013.01)

(58) Field of Classification Search
CPC ......... A61B 6/547; A61B 6/0492; A61B 6/52; A61B 6/5211; A61B 6/5294; A61B 90/39;

(Continued)

(56) References Cited

U.S. PATENT DOCUMENTS 7,497,621 B2 3/2009 Yatesenko et al.
8,625,107 B2 * 1/2014 Kusik .................... G01S 17/74 356/614

(Continued)

FOREIGN PATENT DOCUMENTS

WO 2020095482 A1 5/2020

OTHER PUBLICATIONS

International Search Report, Corresponding to PCT/EP2020/065040, filed May 29, 2020, 14 pages.

(Continued)

*Primary Examiner* — David J Makiya
*Assistant Examiner* — Soorena Kefayati
(74) *Attorney, Agent, or Firm* — Tucker Ellis LLP

(57) ABSTRACT

A computer-implemented method of determining a rotational position of an object in a coordinate system of an x-ray imaging device is provided. An x-ray image is generated of an object to which a Moiré marker for x-ray imaging is attached. The Moiré pattern generated by the Moiré marker is analysed and the rotational position of the marker and hence of the object is determined in a calculative manner. The Moiré marker for x-ray imaging includes a pattern which results in a significantly different appearance when being observed from slightly different perspectives. The Moiré marker for x-ray imaging can include two layers with patterns produced by a material that shields x-ray as good as possible, surrounded and spaced apart by material that is highly transparent in x-ray.

18 Claims, 3 Drawing Sheets

(58) Field of Classification Search
CPC .... A61B 2034/2051; A61B 2034/3954; A61B 2034/3966; A61B 2034/397; A61B 2034/3995; A61B 2034/2055; A61B 2034/2057; A61B 2034/2065; A61B 2034/2068; A61B 2034/373; A61B 2034/3983; A61B 2034/3937; G02B 27/60
See application file for complete search history.

(56) References Cited

U.S. PATENT DOCUMENTS

2003/0088179 A1* 5/2003 Seeley .................. A61B 6/487 600/424
2003/0130576 A1* 7/2003 Seeley .................. A61B 90/36 600/426
2004/0233461 A1* 11/2004 Armstrong ................ G01S 5/16 356/620
2006/0115054 A1* 6/2006 Yatsenko ............. A61B 6/4291 378/207
2007/0253541 A1* 11/2007 Sukovic ................. A61B 90/36 378/205
2007/0280508 A1* 12/2007 Ernst ...................... A61B 5/055 382/107
2008/0071420 A1* 3/2008 Guertin .................. A61B 6/547 5/601
2008/0107241 A1* 5/2008 Yatsenko ............... A61B 6/583 378/207
2014/0286477 A1* 9/2014 Ishii ..................... A61B 6/4291 378/62
2016/0113610 A1* 4/2016 Freudenberger ..... A61B 6/4291 378/163
2016/0175064 A1* 6/2016 Steinle ................... A61B 90/39 600/424
2016/0379353 A1* 12/2016 Makifuchi ............. A61B 6/484 382/131
2017/0215823 A1* 8/2017 Ivanov ................... A61B 6/545
2017/0219498 A1* 8/2017 Chtcheprov .......... G01T 1/2978
2018/0279977 A1* 10/2018 Shinden ............... A61B 6/4035
2019/0175942 A1* 6/2019 Stahl ...................... A61B 6/032

OTHER PUBLICATIONS

MPT—Markers, Metria Innovation Inc., retrieved from internet, <https://www.metriainnovation.com/mpt-markers>.

* cited by examiner

MOIRÉ MARKER FOR X-RAY IMAGING

RELATED APPLICATION DATA

This application is a national phase application of International Application No. PCT/EP2020/065040, filed May 29, 2020, the contents of which are incorporated herein by reference.

FIELD OF THE INVENTION

The present invention relates to x-ray imaging. In particular, the present invention relates to a computer-implemented method of determining a rotational position of an object in a coordinate system of an x-ray imaging device, a Moiré marker for x-ray imaging, a marker array with a Moiré marker for x-ray imaging, a system for determining a rotational position of an object in a coordinate system of an x-ray imaging device, the use of a Moiré marker for x-ray imaging and a computer program.

TECHNICAL BACKGROUND

X-ray imaging has become one of the standard imaging technology frequently used in various different medical fields including intra-operative imaging. Moreover, the use of robotic instruments has significantly increased in the recent years, since they enhance the surgical workflow with supporting x-ray device positioning, imaging and verification. State of the art x-ray imaging devices developed by e.g. the applicant of the present application, i.e. the Brainlab AG, is the x-ray imaging device called Loop-X, as can be gathered from e.g. https://www.brainlab.com/surgery-products/overview-platform-products/robotic-intraoperative-mobile-cbct/. Such state of the art x-ray imaging devices can independently move the detector and source and hence can position the isocenter at the region of interest enabling extra large dynamic field of view and non-isocentric imaging. Such devices can drive autonomously to stored parking and scanning positions, which can all be controlled by the medical practitioner.

However, robotic instruments need to be accurately aligned to a predetermined trajectory or the alignment of such an instrument using robotics must be verified. Furthermore, it is desired to be able to track the position of a non-rigidly fixed body part like for example a vertebra. Nowadays, typically external tracking systems are used for tracking movements of robotic instruments in relation to e.g. the x-ray imaging device. However, if such an external tracking system is used for tracking, generated x-ray images must be registered to said external tracking system. This purpose has been achieved so far by registering the x-ray imaging device coordinate system to the external tracking system or by using marker structures typically consisting of spherical x-ray opaque markers that are typically imaged from predominantly orthogonal projections.

However, the inventors of the present invention have found it disadvantageous that the previous solutions either make an external tracking system, e.g. an optical tracking system, necessary or that multiple images need to be recorded, which includes significant movement of the image source and detector. This leads to a potential collision danger, takes time and increases the x-ray dose to the patient, or the marker structure needs to be very large in order to achieve good accuracy in all dimensions, which in turn might obstruct the surgical field. Based on these findings about the disadvantages of the prior art, the inventors have made the present invention.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given, which shall not be understood to limit the invention only to the features or a combination of the features described in this section.

The inventors of the present invention have found that the use of a Moiré marker for x-ray imaging provides particular advantages. When using a Moiré marker, which, when being imaged with an x-ray beam, generates a Moiré pattern of x-ray signal intensity on/in the x-ray image, said Moiré pattern can be used to determine the rotational position of the object to which the Moiré marker is attached during the generation of the image. This can allow a very convenient and cheap solution for determining a rotational position of the object in the coordinate system of the x-ray imaging device thereby avoiding not only an external tracking system, but also avoiding significant movement of the image source and detector, which entails a potential collision danger. As will become apparent from the present disclosure, the present invention also allows for a high angle resolution when determining said rotational position. Using a Moiré marker for x-ray imaging according to the present invention also reduces the time needed for determining the rotational position of the object to which the marker is attached and it can decrease the x-ray dose to the patient, since only one or at least only a few x-ray images are needed, as will be described hereinafter in more detail. The present invention can use a compact marker structure for x-ray imaging that allows to estimate the position of the marker in the x-ray machine coordinate system very accurately from only one x-ray image.

Said Moiré marker for x-ray imaging and the computer-implemented method of determining the rotational position of the object in the coordinate system of the x-ray imaging device can be used in various different applications. For example, the marker and the method can be used in order to align a robotic instrument accurately to a predetermined trajectory. The marker and the method can also be used to verify the alignment of a medical instrument. The Moiré marker for x-ray imaging of the present invention can also be used as a reference structure in order to track the position of a non-rigidly fixed body part like for example a vertebra. Another potential application is the registration of the x-ray image with respect to an external tracking system by creating a hybrid reference containing a Moiré marker as presented herein in combination with a conventional, i.e. a non-Moiré, x-ray marker. These embodiments and advantageous applications of the present invention will be elucidated hereinafter in more detail.

When generating an x-ray image with a Moiré marker according to the present invention, a Moiré pattern of x-ray signal intensities is generated in/on the image. Such a Moiré pattern is indicative for an angle between the Moiré marker and the x-ray propagation direction of the x-ray imaging device. An automatic, i.e. computer-implemented, analysis of this Moiré pattern allows for the determination of the rotational position of the marker and thus of the object to which the marker is attached in the coordinate system of the x-ray imaging device during imaging. As will become apparent from the following disclosure, the Moiré marker may have at least two different kinds of pattern structures to enlarge the working range with respect to the angle resolution. As will be described in detail, the Moiré marker of the present invention and the corresponding method can be designed to have a proper small angle resolution and can also be designed to have a proper large angle resolution. Further explanations will be provided hereinafter e.g. in the context of the embodiment of FIG. 4.

The disclosed computer-implemented method of determining the rotational position of the object in the coordinate system of the x-ray imaging device comprises the provision of such an x-ray image of the object to which a Moiré marker of the present invention is attached. Since the Moiré marker generates a signal intensity distribution on/in the x-ray image, which intensity distribution is angle-dependent and which is known beforehand, it can be calculated and thus determined at which angle the marker and hence the object to be imaged were positioned with respect to the x-ray source/beam and the x-ray detector when the image was made.

Further details about the computer-implemented method, the Moiré marker for x-ray imaging, the system for determining a rotational position of an object in a coordinate system of an x-ray imaging device, the use of a Moiré marker in x-ray imaging and the computer program element will be described in detail now.

GENERAL DESCRIPTION OF THE INVENTION

In this section, a description of the general features of the present invention is given for example by referring to possible embodiments of the invention.

Technical terms are used herein by their common sense. If a specific meaning is conveyed to certain terms, definitions of terms will be given in the following in the context of which the terms are used.

According to a first aspect of the present invention, a computer-implemented method of determining a rotational position of an object in a coordinate system of an x-ray imaging device is presented. The method comprises the steps of providing one x-ray image of the object, to which a Moiré marker for x-ray imaging is attached. The x-ray image being imaged by the x-ray imaging device. The Moiré marker for x-ray imaging generates a Moiré pattern of x-ray signal intensities on the x-ray image. The Moiré pattern is indicative for an angle between the Moiré marker and the x-ray propagation direction of the x-ray imaging device. The method further comprises the step of determining, based on the Moiré pattern of signal intensities, the rotational position of the object in the coordinate system of the x-ray imaging device.

It should be noted, that in the context of the present invention, the provision of the at least one x-ray image of the object can be seen as generating such an x-ray image. However, this also covers the data acquisition, which is carried out by e.g. a computer when retrieving said x-ray imaging data from e.g. an external entity like a medical recording system or the like. Thus, the term "providing one x-ray image of the object" shall be understood broadly in the context of the present invention and is not limited to the generation of such an x-ray image, but comprises such a generation of an x-ray image of an object only as one embodiment.

It should be noted that the x-ray propagation direction is understood by the person skilled in the art as the spatial direction in which the electromagnetic x-ray energy is propagating from the source to the detector.

The step of "determining the rotational position of the object" can be carried out in various different manners. One preferred embodiment is to select, automatically and/or manually, at least one point in the Moiré pattern and then use a pre-defined mathematical relation between the Moiré pattern of signal intensities and the angle between the Moiré marker and the x-ray propagation direction of the x-ray imaging device for the angle determination. Such a relation can be gathered from for example the embodiment explained in FIG. 3. However, such a determination of the rotational position could also be done by for example comparing the generated Moiré pattern in the x-ray image with a target pattern that was for example previously generated and is stored on a storage unit of a computer. Depending on such a comparison, the computer can determine by means of software/an image processing algorithm what kind of rotational position the marker and hence the object to which the marker is attached was present when the x-ray image was generated.

The method as present herein facilitates a convenient and reliable determination of the rotational position of the object in the coordinate system of the x-ray imaging device, avoids any external tracking system, and avoids movements of the image source and detector, leading to a reduced collision danger caused by said elements of the x-ray imaging device. This enhances the operational safety when determining the position of an object with respect to the three spatial rotational axis within the coordinate system of the x-ray imaging device.

Depending on what kind of structured Moiré marker will be used, the method can be particularly applied with a focus on a very high angle resolution of small angles and can be particularly applied with a focus on a very high angle resolution of large angles.

The present invention can use a compact marker structure for x-ray imaging and allows estimating the position of the marker in the x-ray machine coordinate system very accurately from only one x-ray image. This compact marker structure shall be understood as the Moiré marker for x-ray imaging according to the present invention. Such a Moiré marker for x-ray imaging comprises a pattern, which results in a significantly different appearance when being observed from slightly different perspectives. In an embodiment, said Moiré marker for x-ray imaging consists of two layers with patterns produced by a material that shields x-ray as good as possible like for example lead, surrounded and spaced apart by material that is highly transparent in x-ray like air or like plastics. Other material combinations will be described in detail hereinafter. The size of the openings in the pattern is preferably small compared to the distance of the two levels of the patterns such that a small change in orientation of the Moiré marker results in fairly significant change in the structure of the second layer seen through the aperture of the first layer. An example is to use 0.5 mm openings with a layer distance of 25 mm.

According to another exemplary embodiment of the present invention, the step of determining the rotational position of the object comprises determining at least one point in the Moiré pattern of x-ray signal intensities. The method further comprises the step of using the determined at least one point as an input of a pre-defined relation describing a dependency of the Moiré pattern from the angle between the Moiré marker and the x-ray propagation direction of the x-ray imaging device.

The determination of the at least one point in the Moiré pattern may be done automatically by computer software. For example, the determined at least one point may represent an x-ray signal intensity minimum or an x-ray signal intensity maximum of the Moiré pattern. In other words, at least one point is automatically identified in the generated Moiré pattern of signal intensities and this determined point is used as an input for the mathematical relation that allows the calculation of the three rotational parameters that uniquely define the rotational position of the marker and hence of the object in the coordinate system of the x-ray imaging device. As clear to the skilled reader, also two, three, four or even more points could be determined and used as input for the mathematical relation. For example, two minima and two maxima could be identified and used for the rotational angle determination/calculation. The more points are used, the higher is the accuracy of the determination.

In correspondence to this computer-implemented mathematical method, the present invention provides for a measurement system, which is configured for determining a rotational position of an object by analyzing an x-ray image with such a Moiré pattern of x-ray signal intensities caused by the Moiré marker when being imaged with the x-ray imaging device.

According to another exemplary embodiment of the present invention, the relation is a stored x-ray intensity distribution detected by the x-ray sensor of the x-ray imaging device as a function of the angle between the Moiré marker and the propagation direction of the x-ray imaging device.

The stored x-ray intensity distribution may be stored in e.g. a storage unit within the system carrying out the method of the present invention, but can also be stored, for example, in an external entity like an external data storage unit or for example in a cloud to which the system of the present invention connects for carrying out the corresponding method. Such a mathematical relation/dependency can be gathered from FIG. 3.

According to another exemplary embodiment of the present invention, the method comprises the step of generating a control signal based on the result of the determination of the rotational position of the object. This control signal can be used for positioning the imaged object relative to the x-ray imaging device.

As will become apparent from the exemplary embodiment described in the context of FIG. 4, such a method can be repeated until a pre-defined position condition describing a desired position of the object in the coordinate system of the x-ray imaging device is reached. In other words, this method embodiment can be repeated until a target position of the object is achieved and no further movement or repositioning of the imaged object needs to be done.

According to another exemplary embodiment of the present invention, the object is a medical robot, a medical instrument, a medical device, a patient support device like for example a patient couch, and/or a patient. The method further comprises the step of using the generated control signal to cause a movement of the object.

Using the compact Moiré marker for x-ray imaging of the present invention allows the estimation or precise determination of the rotational position of the marker in the x-ray machine coordinate system on a very accurate level. The inventors of the present invention have found that it is possible to already determine the rotational position with only one x-ray image when using the present invention.

As is clear to the skilled reader, this embodiment of the method can be used to align a robotic instrument, a medical instrument, a medical device, a patient support device like for example a patient couch or the patient himself accurately to a predetermined trajectory relative to the x-ray imaging device. The method can also be used to verify the alignment of such an object.

According to another exemplary embodiment of the present invention, the x-ray image is an x-ray projection image. Furthermore, the step of determining the rotational position of the object takes into account, in a calculative manner, the spatial divergence of the x-ray beam emitted by the x-ray imaging device when doing such x-ray projection images.

As is clear to the skilled reader and is described in the context of the non-limiting exemplary embodiment of FIG. 1, the x-ray beams propagate in a divergent manner from the x-ray source to the x-ray detector. Since this divergence of the beam in space is previously known, this divergence can be compensated for when determining the spatial position of the object by using the method of the present invention. As can be seen in FIG. 1, the structural elements of the Moiré marker 101 that are further away from the axis that virtually connects the x-ray source 107 and the x-ray detector 109 have a different angle with respect to the x-ray propagation direction as compared to the elements of the Moiré marker that are positioned along the virtual axis connecting the source and detector. Further details will be described in the context of other embodiments hereinafter.

According to another exemplary embodiment of the present invention, in the provided x-ray image not only the Moiré marker, but also a further marker is attached to the object. Both markers are used as a marker array. And the method comprises the automatic identification of the further marker in the provided x-ray image.

In other words, a second, non-Moiré marker for coarsely finding in the x-ray image the position of the Moiré pattern is introduced.

In a preferred embodiment, the further, non-Moiré marker is of an x-ray opaque material and preferably has a ball shape, a cuboid shape, a pyramidal shape, a disc shape, or any combination thereof. Such a conventionally shaped, further marker, i.e. a non-Moiré marker, allows, for example by means of an automatic image software analysis, to detect and locate where the Moiré pattern is located within the x-ray image. In particular, in certain instances, the Moiré pattern may not be easily found with software analysis or manually by a user and in such situations, the further, non-Moiré marker facilitates a fast coarse identification of the location of the Moiré pattern within the provided x-ray image.

According to another exemplary embodiment of the present invention, the method further comprises the step of using the automatically identified further marker in the provided x-ray image for calculating a translational position (X, Y, Z) of the Moiré marker within the coordinate system of the x-ray imaging device.

In other words, the identification of the further marker can be used for determining the translational position (X, Y, Z) of the marker in the coordinate system of the x-ray imaging device.

As is clear to the skilled reader, the Moiré marker and the second marker are in a pre-defined spatial relationship. By identifying the further marker in the x-ray image, one can coarsely identify the position of the marker array and thereby derive the region of the x-ray image in which the Moiré pattern is expected to be found, because it is known that the Moiré marker was projected the same way. The overall six-dimensional position of the marker array (including three rotational degrees of freedom and three translational degrees of freedom X, Y and Z) is best determined using for example a numerical optimization method for optimizing all dimensions at the same time. This holds true because a slight tilt will cause the second marker structure to be slightly smaller, which can be easily mistaken with a translation in the Z dimension, while a small translation in X/Y will cause a change in angulation, which can be easily mistaken as a slight rotation of the marker when looking at the Moiré pattern.

According to another exemplary embodiment of the present invention, the step of determining the rotational position comprises a comparison between at least the Moiré pattern of the x-ray signal intensities generated by the Moiré marker in the x-ray image with a target pattern of x-ray intensities to be generated by the Moiré marker.

In other words, in this embodiment, the generated Moiré pattern is compared with a target pattern without calculating an angle value. The actual pattern can be compared with the previously defined target pattern, and in case the optical appearance of the patterns do not match, or do not match to a certain, previously defined threshold, the system carrying out this method may then generate a control signal to steer or control a movement of the object that is imaged. This can be repeated until the optical appearance of the two patterns, the Moiré pattern in the actual x-ray image and the target pattern, do match to certain, predefined acceptable extent.

This embodiment is in contrast to some previously described embodiments where a particular angle value is determined in a calculative manner. An exemplary embodiment was discussed based on the non-limiting example shown in FIG. 3.

According to another exemplary embodiment of the present invention, the previously described embodiment is repeated until a pre-defined match between the generated Moiré pattern in the provided x-ray image and the target image is achieved.

It should be noted that this comparison might be done purely based on an optical comparison. In other words, the generated Moiré pattern and the target pattern may be compared with respect to their visual appearance. However, also a detailed analytical comparison between these two patterns shall be comprised by the presented embodiment.

According to another exemplary embodiment of the present invention, the method further comprises the step of automatically detecting the Moiré pattern of x-ray signal intensities in the x-ray image with an image process algorithm.

In other words, this embodiment describes that image processing algorithms can be used to automatically localize the Moiré pattern within the provided x-ray image.

According to a second aspect of the present invention, a Moiré marker for x-ray imaging is presented. The Moiré marker comprises a pattern structure of at least a first and a second material, wherein the first material has a higher x-ray opacity than the second material. The pattern structure of the first and the second material is configured for generating a Moiré pattern of x-ray signal intensities in an x-ray image when being imaged by an x-ray imaging device.

As is clear to the skilled reader, such a Moiré marker is understood as an object, which, when being imaged with an x-ray beam, generates a Moiré pattern of x-ray signal intensity on/in the x-ray image. Said Moiré pattern allows for determining the rotational position of the object to which the Moiré marker is attached during the generation of the image.

As was mentioned before, the Moiré marker comprises a "pattern structure". In other words the Moiré marker is structured with any kind of pattern using at least the two materials, which are different with respect to x-ray opacity, which results in a significantly different appearance when being imaged with x-rays from slightly different perspectives.

The Moiré marker may have one, two or more layers of such a pattern structure. It should be noted that the term "layer" shall be understood as one volume, i.e. one spatial zone, of the marker, in which the elements that constitute the pattern structure are located.

In other words, an x-ray marker is presented that comprises a pattern, which results in a significantly different appearance when being observed from slightly different perspectives. One prominent implementation would be that the marker consists of two layers with patterns produced by a material that shields x-ray as good as possible like for example lead (half-value thickness of lead with x-ray of 100 kV is 0.27 mm), surrounded and spaced apart by material that is highly transparent in x-ray like air or like plastics. Other material combinations will be described in detail hereinafter. The size of the openings in the pattern is preferably small compared to the distance of the two levels of the patterns such that a small change in orientation of the Moiré marker results in fairly significant change in the structure of the second layer seen through the aperture of the first layer. An example is to use 0.5 mm openings with a layer distance of 25 mm.

It should also be noted that between different layers of the Moiré marker, see e.g. the embodiment 101 shown in FIG. 1, a material in the area of diameter $d_1$ can be used that is different from the material with "high x-ray opacity" and the "material with low x-ray opacity", as will be explained in detail hereinafter.

However, multiple structures with different hole sizes and layer distances can be used to have a larger working range while maintaining accuracy. This will be explained in more detail in the context of particular embodiments hereinafter.

In addition to these patterns, which are used to determine the rotation, the marker may include more common features such as spheres that allow for an accurate determination of the other spatial dimensions (X, Y, Z).

It should be noted that a single layer of such structure also works, but double layer Moiré markers for x-ray imaging are more sensitive to more angle deviations. A single layer embodiment is shown on the right-hand side of FIG. 2, whereas a double layer embodiment of the Moiré marker for x-ray imaging according to the present invention is shown in the embodiment on the left-hand side of FIG. 2. Other than the fact that one marker is a single layer version and the other is a double layer version of the Moiré marker for x-ray imaging of the present invention, the two markers of FIG. 2 are identical. Moreover, it should be noted that the double layer Moiré marker for x-ray imaging shown in FIG. 2 on the left hand side, is schematically identical to the double layer Moiré marker for x-ray imaging shown in FIG. 1.

In order to detect the Moiré marker, the x-ray image can be captured and inspected for the location of the further, non-Moiré marker, which may be a spherical marker in a non-limiting example. From this position, the position of the representation of the structural pattern can be deduced and the orientation of the marker can be determined from the distribution of the x-ray signal intensities in the Moiré pattern captured in the x-ray image.

It should be noted that the term "material with high x-ray opacity" shall be understood as an x-ray opaque material and "material with low x-ray opacity" an x-ray non-opaque material. Exemplary materials and combinations thereof will be described hereinafter.

According to another exemplary embodiment of the invention, the pattern structure of the first and the second material is configured for allowing a determination of a rotational position of the Moiré marker from the x-ray image of the Moiré marker.

In other words, this embodiment describes the characteristics of the generated Moiré pattern of signal intensity, namely that it allows for the determination of the rotational angle of the marker and, as a consequence, of the object to which the marker is attached. As has been described hereinbefore in detail, the generated Moiré pattern is dependent on the angle between the Moiré marker and the x-ray imaging device, in particular between the Moiré marker and the propagation direction of the beams emitted by the x-ray imaging device.

According to another exemplary embodiment of the present invention, the Moiré marker has a pattern structure, which comprises a first layer with a first pattern of the first material and the second material and comprises a second layer with a second pattern of the first material and the second material.

A non-limiting example of this embodiment is depicted on the left-hand side of FIG. 2 and is also shown in the embodiment of FIG. 1. This embodiment may be described in that the Moiré marker for x-ray imaging has a first layer with a pattern of x-ray opaque material with gaps in between and has a second layer with a pattern of x-ray opaque material also with gaps in between. The size of the openings in the pattern shall be small compared to the distance between the two layers such that a small change in orientation of the Moiré marker results in a fairly significant change in the structure of the second layer seen through the aperture of the first layer.

According to another exemplary embodiment of the present invention, the first layer and the second layer are separated from each other by a first distance $d_1$. In the first pattern, and preferably also in the second pattern, the second material has a first width $w_1$ between two adjacent pattern elements of the first material. Moreover, the first distance $d_1$ is larger than the first width $w_1$.

This embodiment of the Moiré marker ensures that a proper resolution for small angle changes is provided. As will be elucidated with the non-limiting example of the embodiment shown in FIG. 1, the distance $d_1$ between the first and the second layer may be much larger as compared to the width of the gap between the elements of the first layer, which block the x-ray beams of the x-ray source. This relationship between $d_1$ and $w_1$ can be easily retrieved from the FIG. 1 example.

According to another exemplary embodiment of the present invention, the pattern structure, further comprises a third layer with a third pattern of the first and second material, and a fourth layer with a fourth pattern of the first and second material, wherein the third layer and the fourth layer are separated from each other by a second distance $d_2$. The third pattern, and preferably also in the fourth pattern, the second material has a second width $w_2$ between two adjacent pattern elements of the first material. Moreover, the second distance $d_2$ is larger than the width $w_2$ and the ratio $w_1/d_1$ is different from a ratio $w_2/d_2$.

With this embodiment, it is ensured that the Moiré marker has at least two different kinds of pattern structures such that one enlarges the working range with respect to angle resolution. This is generally described with four layers and it is apparent to the skilled reader that the first and second layer will generate a first Moiré pattern and the third and fourth layer will generate a second Moiré pattern in the x-ray image. The patterns have different parameters, $d_1$, $w_1$ versus $d_2$, $w_2$, and are thus specifically useful for different angle values, i.e. good for a proper small angle resolution versus good for a proper large angle resolution. Therefore, by providing a Moiré marker which generates such two different Moiré patterns, the working range is enlarged.

Note that the third and fourth layers may also be comprised in a second Moiré marker for x-ray imaging, which can be used in combination with the first Moiré marker for x-ray imaging having the first and second layers. In other words, a marker array comprising two different Moiré markers for x-ray imaging can be beneficially provided. In such a case, the first and second marker should be positioned according to a predefined relation, like e.g. adjacent to each other as shown in FIG. 5E, and/or angled to each other as depicted in FIG. 5C, and/or the first marker is provided within the second marker as depicted in FIG. 5D, or the other way around. Thus, one may also use a combination of two Moiré markers wherein the first Moiré marker has the first pattern structure with the first and second layer and the second Moiré marker has a second structure with a third and fourth layer.

It is of course not excluded, that the first and second layer use a first and second material and that the third and fourth layer use a third and fourth material, which are different from the first and second material. This is also disclosed herewith as a particular embodiment of the Moiré marker for x-ray imaging according to a particular embodiment.

According to another embodiment of the present invention within one Moiré marker for x-ray imaging all layers are spatially fixed relative to each other and are parallel to each other. In a preferred embodiment thereof, the centers of mass of the layers are located on a virtual axis that extends perpendicular to the layers of the marker.

According to another exemplary embodiment of the present invention, the first material is or comprises lead, tin, bismuth, tungsten, iodine, gold, tantalum, yttrium, niobium, molybdenum, ruthenium, rhodium, barium, lanthanum, cerium, praseodymium, neodymium, samarium, europium, gadolinium, terbium, dysprosium, holmium, erbium, thulium, ytterbium, lutetium, hafnium, rhenium, osmium, iridium, bismuth, or any combination thereof, and wherein the second material is air, plastic material, carbon, a composite of a thermoplastic resin with carbon-fiber reinforcement, a thermoplastic polymer, like e.g. PEEK, or any combination thereof.

According to a third aspect of the present invention, a marker array for x-ray imaging is presented. The marker array comprises a Moiré marker for x-ray imaging according to any of the aspects or embodiments described herein. Moreover, the marker array comprises an x-ray marker of an x-ray opaque material, preferably having a ball shape, a cuboid shape, a pyramidal shape, a disc shape, or any combination thereof.

As has been described hereinbefore, this further x-ray marker, which is not a Moiré marker, but is for x-ray imaging, is used to identify the location of this x-ray marker in the x-ray image. From this identified location, the position of the representation of the structural pattern of the Moiré marker can be deduced and the orientation of the marker can be determined from the distribution of the x-ray signal intensities in the x-ray image. This additional x-ray marker presented in this embodiment may thus be seen as a conventional x-ray marker or fiducial.

According to another aspect of the present invention, a system for determining a rotational position of an object in a coordinate system of an x-ray imaging device is presented. The system comprises a calculation unit which is configured for carrying out the method as presented herein.

In a particular embodiment, the system is part of the x-ray imaging device, or is part of a tracking system, or is part of a calibration system used in the context of x-ray imaging.

According to an exemplary embodiment of the present invention, the system is configured for controlling the position of the object in the coordinate system of the x-ray imaging device. The system comprises the x-ray imaging device and the calculation unit is configured for generating, based on the result of the determination of the rotational position of the object, a control signal for positioning the imaged object relative to the x-ray imaging device.

Preferably, the calculation unit is also configured for using the generated control signal to cause a movement of the object, as has been described hereinbefore in more detail.

According to another exemplary embodiment of the present invention, the system comprises a Moiré marker for x-ray imaging as described herein.

According to another aspect of the present invention, the use of a Moiré marker for x-ray imaging as described herein for determining a rotational position of an object in a coordinate system of an x-ray imaging device is presented.

According to another aspect of the present invention, a program is presented which, when running on a computer or when loaded onto a computer, causes the computer to perform the method steps of the method described herein. This also comprises a program storage medium on which the program is stored, and/or a computer comprising at least one processor and a memory and/or the program storage medium, wherein the program is running on the computer or loaded into the memory of the computer, and/or a signal wave or a digital signal wave, carrying information which represents the program, and/or a data stream which is representative of the program.

The computer program may be part of an existing computer program, but it can also be an entire program by itself. For example, the computer program may be used to update an already existing computer program to get to the present invention. The computer readable medium storing such a program may be seen as a storage medium, such as for example, a USB stick, a CD, a DVD, a data storage device, a hard disk, or any other medium on which a program element as described above can be stored.

In the following definitions are presented as used in the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Navigation System

As has been described before, in one aspect of the present invention, a system for determining a rotational position of an object in a coordinate system of an x-ray imaging device is presented. In an embodiment, this system is a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

These and other features of the invention will become apparent from and elucidated with reference to the description described hereinafter.

BRIEF DESCRIPTION OF THE DRAWINGS

In the following, the invention is described with reference to the appended Figures which give background explanations and represents specific embodiments of the invention. The scope of the invention is however not limited to the specific features disclosed in the context of the figures.

DESCRIPTION OF EMBODIMENTS

Figure 1:
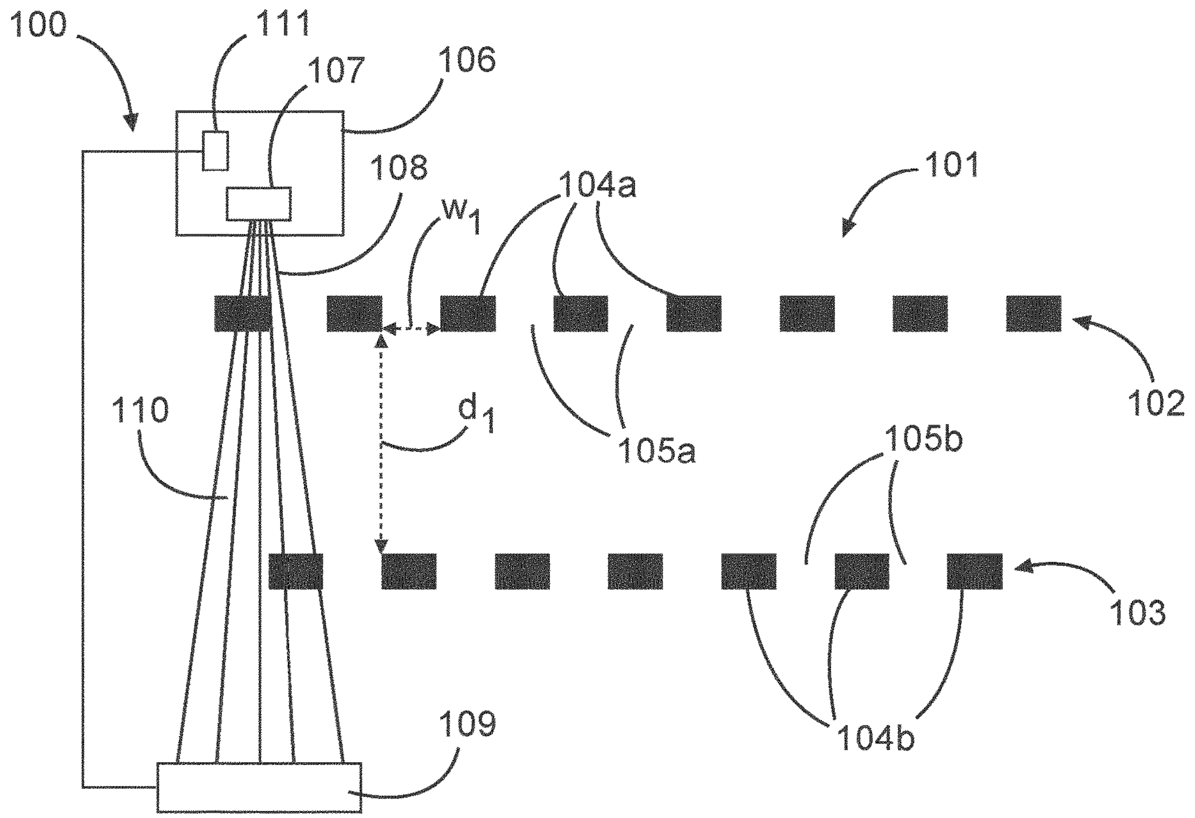
FIG. 1 schematically shows a system for determining a rotational position of an object in a coordinate system of an x-ray imaging device using a Moiré marker for x-ray imaging according to an exemplary embodiment of the present invention.

FIG. 1 schematically shows a system 100 for determining a rotational position of an object in the coordinate system of an x-ray imaging device 106. The x-ray imaging device 106 comprises a calculation unit 111, which is configured for carrying out the computer-implemented method of determining the rotational position of the object in the coordinate system as has been disclosed hereinbefore in detail. In particular, this calculation unit 111 can be provided with an x-ray image of the object to which the Moiré marker 101 is attached. The detector 109 detects the x-ray intensities that result from the propagation of the x-ray beams 108 that are propagating from the x-ray source 107 through the object, not shown here, to which the Moiré marker for x-ray imaging 101 is attached. The Moiré marker 101 generates a Moiré pattern of x-ray signal intensities on the image. The Moiré pattern is indicative for the angle between the Moiré marker 101 and the x-ray propagation direction of the x-ray beams 108. The calculation unit 111 is configured for determining, based on the Moiré pattern of signal intensities, the rotational position of the marker 101 and hence of the object to which the marker is attached in the coordinate system of the x-ray imaging device 106.

As can be gathered from FIG. 1, the x-ray image is an x-ray projection image. Consequently, the determination of the rotational position of the object takes into account, in a calculative manner, the spatial divergence 110 of the x-ray beams 108 emitted by the x-ray imaging device 106. If desired, a further marker, which is a non-Moiré marker, and which is made of an x-ray opaque material and preferably has a ball shape, a cuboid shape, a pyramidal shape, a disc shape or any combination thereof, is also attached to the object and preferably also fixed to the Moiré marker 101. The captured x-ray image can then be expected for the location of the spherical marker. From this position, the position of the Moiré pattern can be deduced and the rotational position of the Moiré marker can be determined from the distribution of the signal intensities, as has been described hereinbefore in detail and will be described in more detail with respect to for example the embodiment of FIG. 3.

As can be seen from FIG. 1, the Moiré marker 101 comprises a pattern structure of at least a first and a second material. The first material has a higher x-ray opacity than the second material. Due to this pattern structure, a Moiré pattern is generated in the x-ray image which allows for the determination of the rotational position of the Moiré marker 101 from the x-ray image that is generated on the detector 109. The pattern structure of the Moiré marker 101 comprises a first layer 102 with a first pattern of the first material 104*a* and a second material 105*a*. A second layer 103 is comprised with the second pattern of the first material 104*b* and second material 105*b*. The first layer 102 and the second layer 103 are separated from each other by a first distance $d_1$.

In the first pattern and preferably also in the second pattern, the second material has a first width $w_1$ between two adjacent pattern elements of the first material. It should be noted, that the first distance $d_1$ is larger than the first width $w_1$ in order to provide for a proper angle resolutions for small angle changes of the angle between the marker and the propagation direction of the x-ray beams 108. It should also be noted that between different layers of the Moiré marker a material in the area of diameter $d_1$ can be used that is different from the material with "high x-ray opacity" and the "material with low x-ray opacity", as will be explained in detail hereinafter. Thus, a third, other material or also a material combination can be used in this section of the marker.

The embodiment of FIG. 1 uses a compact Moiré marker 101 (not shown at scale here) for x-ray imaging and allows estimating the position of the marker in the x-ray machine coordinate system very accurately from only one x-ray image. Such a Moiré marker for x-ray imaging comprises a pattern, which results in a significantly different appearance when being observed from slightly different perspectives. In this embodiment, said Moiré marker 101 for x-ray imaging consists of two layers 102, 103 with patterns produced by a material that shields x-ray as good as possible like for example lead, surrounded and spaced apart by material that is highly transparent in x-ray like air or like plastics. The size of the openings in the pattern is small compared to the distance of the two levels of the patterns such that a small change in orientation of the Moiré marker results in fairly significant change in the structure of the second layer seen through the aperture of the first layer. An example is to use 0.5 mm openings with a layer distance of 25 mm. Moreover, it should be noted that the double layer Moiré marker for x-ray imaging shown in FIG. 1, is schematically identical to the double layer Moiré marker for x-ray imaging shown on the left hand side of FIG. 2, which will be described now in detail.

Figure 2:
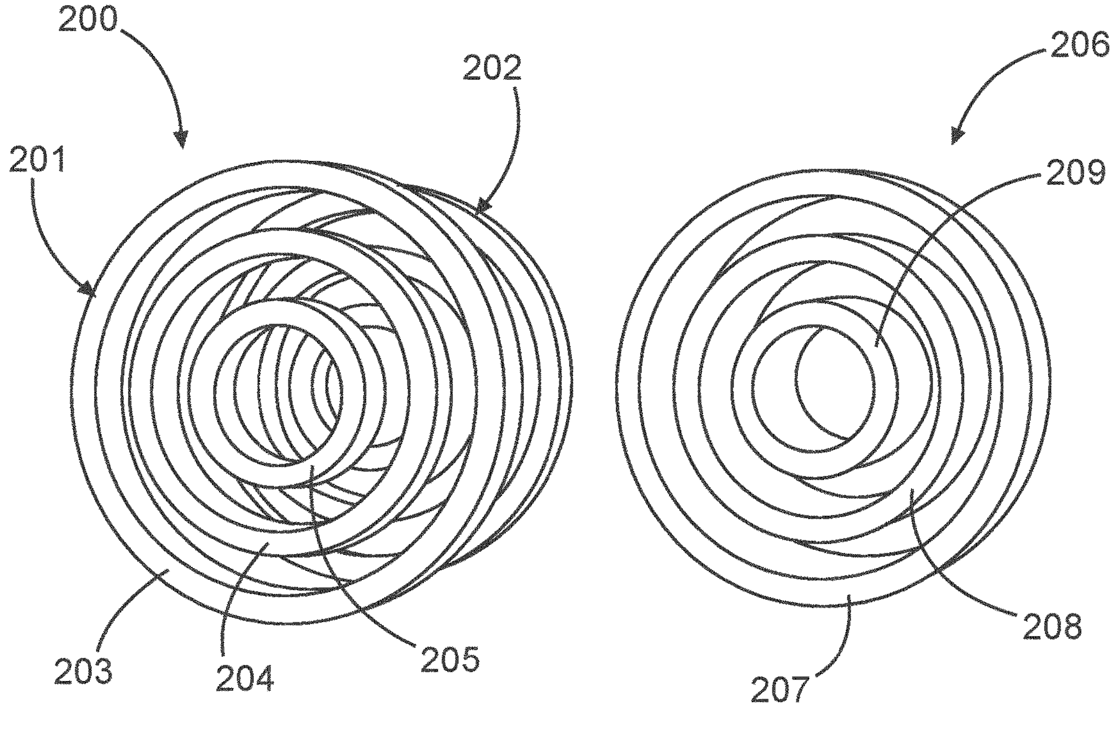
FIG. 2 schematically shows two embodiments of a Moiré marker for x-ray imaging according to two different embodiments of the present invention.

FIG. 2 schematically shows a first Moiré marker for x-ray imaging 200 and a second Moiré marker for x-ray imaging 206. The first Moiré marker 200 comprises a first layer 201 with a first pattern of the first material and the second material and comprises a second layer 202 with a second pattern of the first material and the second material. In particular, the first layer 201 comprises three concentrically arranged rings 203, 204 and 205. They can for example be made of the material lead, tin, bismuth, tungsten, iodide, gold, tantalum, yttrium, niobium, molybdenum, ruthenium, rhodium, barium, lanthanum, cerium, praseodymium, neodymium, samarium, europium, gadolinium, terbium, dysprosium, holmium, erbium, thulium, ytterbium, lutetium, hafnium, rhenium, osmium, iridium, bismuth. The gaps between these concentrically arranged rings may be filled with the second material that could be selected from air, plastic material, carbon, a composite of a thermoplastic resin with carbon-fibre reinforcement, a thermoplastic polymer, like e.g. PEEK, or any combination thereof, to mention only some exemplary embodiments.

The same material combinations can be used also for the single layer Moiré marker for x-ray imaging 206. This Moiré marker comprises only a single layer of a pattern structure, which is made of three concentrically arranged rings 209, 208 and 207.

Figure 3:
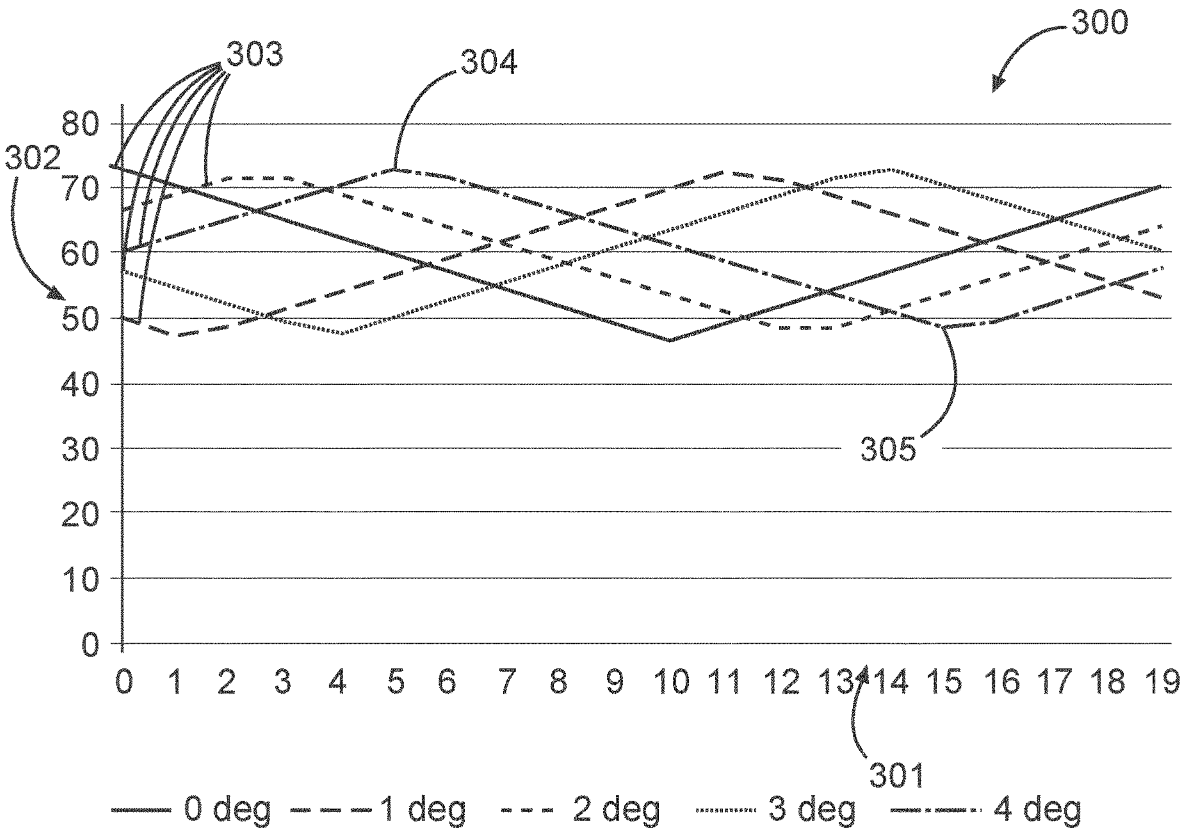
FIG. 3 schematically shows five different Moiré patterns of x-ray signal intensities generated in an x-ray image with a Moiré marker for x-ray imaging according to an exemplary embodiment of the present invention for five different rotational positions of the marker in the coordinate system of the x-ray imaging device.

FIG. 3 schematically shows a diagram where on the x-axis the detector position on the x-ray detector is presented with reference sign 301. The y-axis 302 depicts the detected x-ray intensity. Hence, in FIG. 3, the intensity distribution including the Moiré pattern 300 over the x-ray detector is shown for five different rotational positions of a Moiré marker when being imaged by an x-ray imaging device. In other words, FIG. 3 shows five relations 303 describing the dependency of the Moiré pattern 300 from the angle between the Moiré marker and the x-ray propagation direction of the x-ray imaging device. As can be seen in FIG. 3, the relation 303 respectively comprise x-ray signal intensity minima 305 and x-ray signal intensity maxima 304. The diagram shown in FIG. 3 depicts the x-ray absorption in percent for different marker angles at 500 mm distance to the x-ray source using 0.5 lead with 1 mm hole distance and 25 mm layer distance. In other words, a Moiré marker as shown in FIG. 1 has been used for generating the diagram in FIG. 3.

Figure 4:
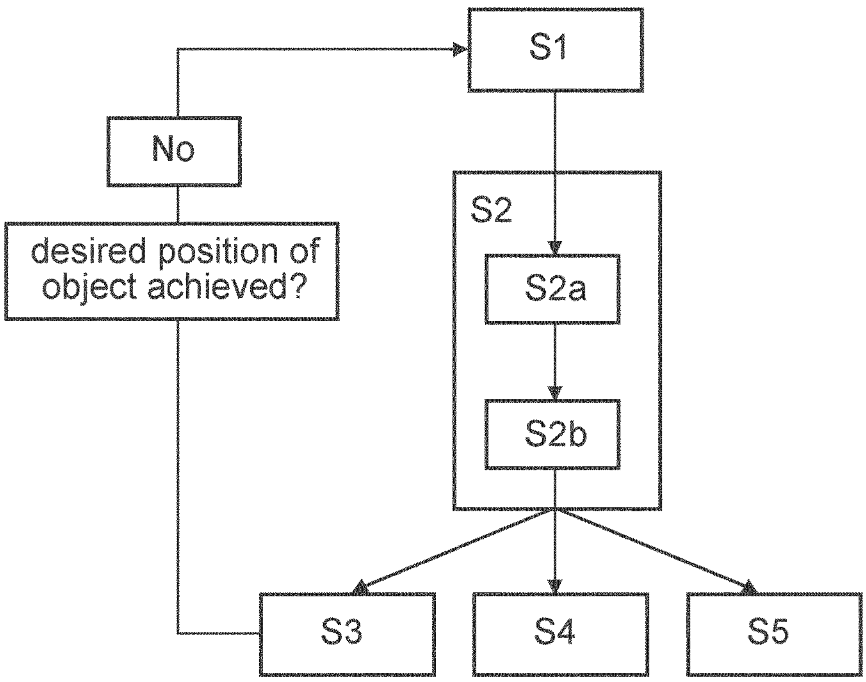
FIG. 4 schematically shows a flow diagram of a computer-implemented method of determining a rotational position of an object in a coordinate system of an x-ray imaging device according to different embodiments of the present invention.

FIG. 4 schematically shows a flow diagram of a computer-implemented method of determining a rotational position of an object in a coordinate system of an x-ray imaging device. The method described in the context of FIG. 4 particularly comprises three different embodiments that can be used separately, but which can also be combined. In particular, the method steps S3, S4 and S5 follow the method steps S1 and S2*a* and S2*b*. This will be described now in more detail.

The method comprises the step of providing at least one x-ray image of the object in step S1. A Moiré marker for x-ray imaging is attached to the object. The Moiré marker for x-ray imaging, as has been described before, generates a Moiré pattern of x-ray signal intensities on the image that is provided. The Moiré pattern is indicative for an angle between the Moiré marker and an x-ray propagation direction of the x-ray imaging device. In step S2, the rotational position of the object in the coordinate system of the x-ray imaging device is determined based on the Moiré pattern of signal intensities in the x-ray image provided. The step S2 comprises the further two sub-steps S2*a* and S2*b*. In particular, at least one point in the Moiré pattern of x-ray signal intensities is determined in the x-ray image during step S2*a*. Moreover, the determined at least one point is used as an input in step S2*b* when putting this determined point into a pre-defined relation describing the dependency of the Moiré pattern from the angle between the Moiré marker and the x-ray propagation direction of the x-ray device. Therefore, the result of step S2 is the determined rotational position of the object. This result can now be used either only for step S3, or only for step S4 or only for step S5, but this can also be combined. In step S3, a control signal for positioning the imaged object relative to the x-ray imaging device is generated based on the result of the determination of the rotational position, i.e. the outcome of method step S2. This control signal can be used to cause a movement of the object, as has been described hereinbefore. For example, a medical robot, a medical instrument, a medical device, a patient support device like a patient couch and/or the patient may be moved based on the use of this control signal. It may be checked after step S3 whether the desired position of the object is already achieved. If this is denied, then the method comprising steps S1, S2 and S3 can be repeated until a pre-defined position condition describing the desired position of the object in the coordinate system of the x-ray imaging device is reached. Alternatively or also in addition, the result of the method step S2 can also be used to verify the alignment of a medical instrument in step S4. However, in step S5, one could also use the outcome of the step S2, i.e. the determined rotational position of the marker and of the object for tracking an object during for example image guided surgery. This is depicted in FIG. 4 by reference sign S5.

FIGS. 5A to 5E schematically show five embodiments of one or two Moiré markers for x-ray imaging, which can of course be combined which each other. As was described before and as will become apparent from the detailed description of the embodiments of FIGS. 5A to 5E, within one Moiré marker for x-ray imaging all the layers are spatially fixed relative to each other, all the layers are parallel and preferably the centres of mass of the layers are located on a virtual axis that extends perpendicular to the layers of the marker.

Figure 5A:
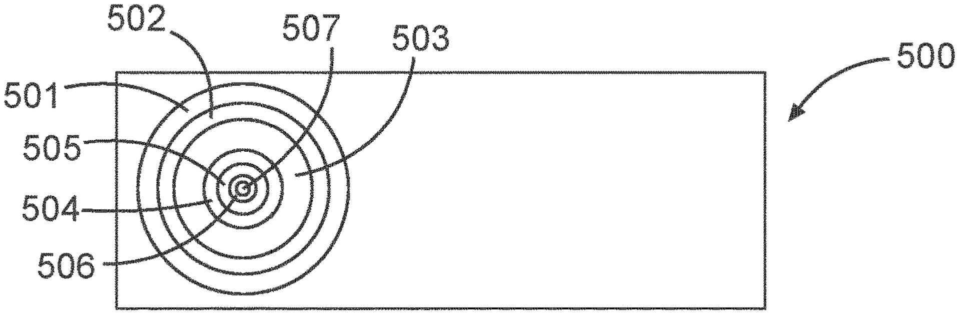
FIGS. 5A to 5E schematically show five embodiments of the present invention, in which one or more Moiré marker for x-ray imaging are depicted.

FIG. 5A shows a top view of one Moiré marker 500 for x-ray imaging, which comprises two layers with a non-periodic pattern. However, in this top view only the first layer, i.e. the top layer, can be seen. The skilled reader will appreciate that the second layer of the Moiré marker 500 is located below this first layer, as can be gathered for example from the cross sectional view of FIG. 1, in which both layers of a similar Moiré marker with two layers is depicted. The Moiré marker 500 comprises a pattern structure within said first and second layer using a first and a second material, wherein the first material has a higher x-ray opacity than the second material. The pattern structure in the first layer shown in FIG. 5A is provided by 6 concentrically arranged rings 501-506 and one central element 507, wherein rings 501, 503 and 505 and the central element 507 are made of the first material, whereas rings 502, 504 and 506 are made of the second material. As is clear from FIG. 5A, the pattern per layer is not periodic, since the respective widths of the rings are different.

Figure 5B:
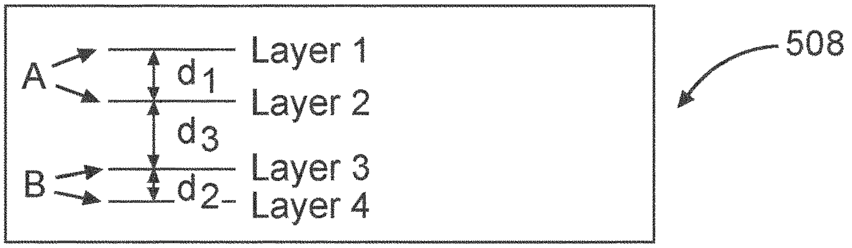

FIG. 5B shows a cross sectional view through a Moiré marker 508 for x-ray imaging with four layers according to another embodiment of the present invention. It comprises layer 1 and layer 2, which are separated from each other by distance $d_1$, as well as layer 3 and layer 4, which are separated from each other by distance $d_2$, which is different from distance $d_1$. Each layer of layer 1 to layer 4 comprises a periodic or non-periodic pattern made at least of the first and second material that have been described hereinbefore in detail. Layers 2 and 3 are separated from each other by distance $d_3$, which is different from distances $d_1$ and $d_2$.

Figure 5C:
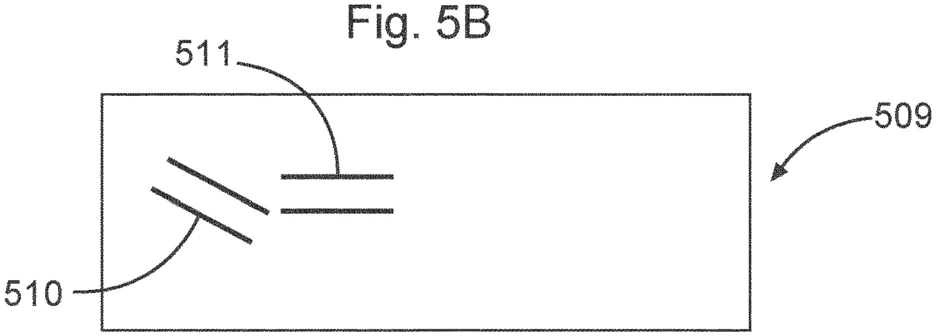

As was described hereinbefore, the present invention of course also covers the use of a combination of two or more Moiré markers for x-ray imaging. Thus, FIG. 5C shows a marker array 509 comprising a first and a second Moiré marker 510, 511 for x-ray imaging as two different and separated objects, which are however provided in a fixed position to each other. They may e.g. be mounted to a fixation element. As can be seen from FIG. 5C, the two markers 510, 511 are not positioned in parallel to each other, but in an angled configuration. The skilled person appreciates that both markers 510, 511 can be chosen to be identical in their geometrical design and in the materials used. But of course also a combination of two Moiré markers 510, 511 using for example different pattern structures, e.g. different distances between the two layers, and/or different materials with different x-ray opacity is part of the present invention.

Figure 5D:
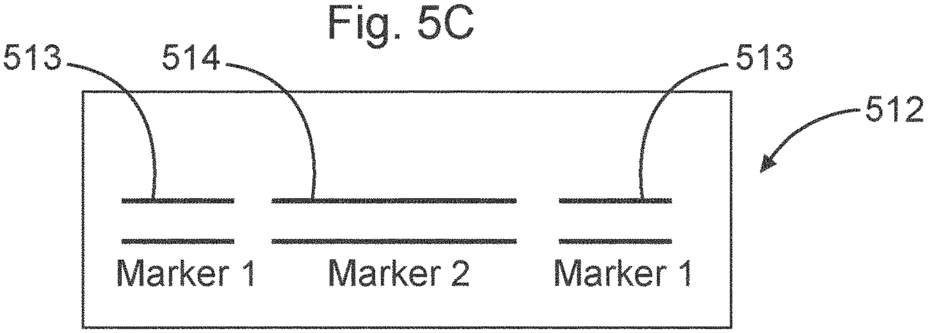

FIG. 5D shows in a cross sectional view 512 a first Moiré marker for x-ray imaging 513 ("Marker 1"), which houses a second Moiré marker for x-ray imaging 514 ("Marker 2"). In other words, the second marker 514 is provided within, i.e. integrated in, the first marker 513, which circumvents with a ring shape the second marker 514. As can be seen from the cross section in FIG. 5D, both markers have a double layer structure.

Figure 5E:
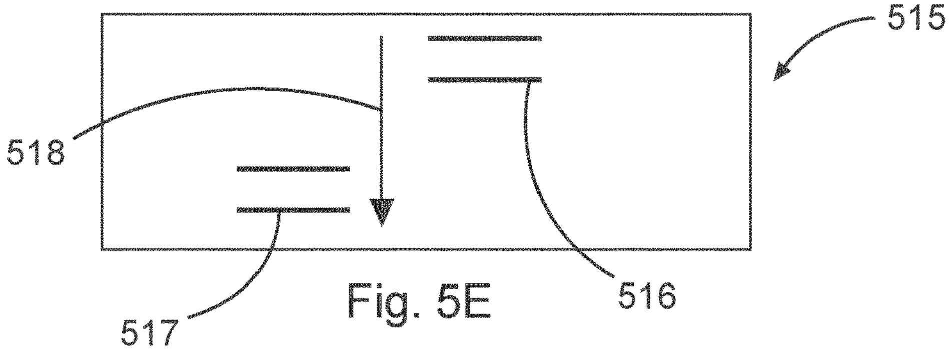

FIG. 5E shows a marker array 515 comprising two double layer Moiré markers for x-ray imaging 516, 517 according to another embodiment of the present invention. The markers 516, 517 are located at positions along the x-ray propagation direction 518, in which the distance between the markers is ≥0. The two markers can thus have a distance along the x-ray propagation direction 518, or can alternatively positioned next to each other, i.e. at the same height along the x-ray propagation direction 518. The Moiré markers 516, 517 are two different objects, which are however provided in a predetermined, fixed position to each. This can be realized e.g. by mounting them onto a fixation element.

Other variations to the disclosed embodiments can be understood and effected by those skilled in the art in practicing the claimed invention, from the study of the drawings, the disclosure, and the appended claims. In the claims, the word "comprising" does not exclude other elements or steps and the indefinite article "a" or "an" does not exclude a plurality. A single processor or other unit may fulfil the functions of several items or steps recited in the claims. The mere fact that certain measures are recited in mutually different dependent claims does not indicate that a combination of these measures cannot be used to advantage. A computer program may be stored/distributed on a suitable medium such as an optical storage medium or a solid-state medium supplied together with or as part of other hardware, but may also be distributed in other forms, such as via the Internet or other wired or wireless telecommunication systems. Any reference signs in the claims should not be construed as limiting the scope of the claims.

The invention claimed is:

1. A computer-implemented method of determining a rotational position of an object in a coordinate system of an associated x-ray imaging device, the method comprising:

providing an x-ray image of an object to which a Moiré marker for x-ray imaging is attached during generation of the x-ray image, the x-ray image having been generated when the object to which the Moiré marker for x-ray imaging is attached is imaged together with the Moiré marker for x-ray imaging by the associated x-ray imaging device, wherein a Moiré pattern of x-ray signal intensities is generated on the x-ray image by the Moiré marker for x-ray imaging when the object to which the Moiré marker for x-ray imaging is attached is imaged together with the Moiré marker for x-ray imaging by the associated x-ray imaging device, wherein the Moiré pattern of x-ray signal intensities generated when the object other than the associated x ray imaging device-to which the Moiré marker for x-ray imaging is attached is imaged together with the Moiré marker for x-ray imaging by the associated x-ray imaging device is indicative of an angle between the Moiré marker for x-ray imaging and an x-ray propagation direction of the associated x-ray imaging device in the coordinate system of the associated x-ray imaging device, wherein the object comprises one or more of: a medical robot, a medical instrument, a medical device, a patient support device, and/or a patient;

determining, based on the Moiré pattern of x-ray signal intensities generated when the object to which the Moiré marker for x-ray imaging is attached is imaged together with the Moiré marker for x-ray imaging by the associated x-ray imaging device, the rotational position of the object in the coordinate system of the associated x-ray imaging device;

generating a control signal for positioning the object relative to the x-ray imaging device based on the determined rotational position of the object; and repeating the steps of providing the x-ray image of the object, determining the rotational position of the object, and generating the control signal until a pre-defined position condition describing a desired position of the object in the coordinate system of the x-ray imaging device is reached.

2. The method according to claim 1, wherein the determining the rotational position of the object comprises:

determining at least one point in the Moiré pattern of x-ray signal intensities; and using the determined at least one point as an input of a pre-defined relation describing a dependency of the Moiré pattern from the angle between the Moiré marker and the x-ray propagation direction of the x-ray imaging device.

3. The method according to claim 1, further comprising:

using the generated control signal to cause a movement of the object.

4. The method according to claim 1, wherein the x-ray image is an x-ray projection image, and the determined rotational position of the object takes into account, in a calculative manner, a spatial divergence of an x-ray beam emitted by the x-ray imaging device.

5. The method according to claim 1, further comprising:

automatically detecting the Moiré pattern of x-ray signal intensities in the x-ray image with an image processing algorithm.

6. The method according to claim 2, wherein the determined at least one point represents an x-ray signal intensity minimum of the Moiré pattern or an x-ray signal intensity maximum of the Moiré pattern.

7. The method according to claim 2 wherein the pre-defined relation is a stored x-ray intensity distribution detected by an x-ray sensor of the x-ray imaging device as a function of the angle between the Moiré marker and the x-ray propagation direction of the x-ray imaging device.

8. A computer-implemented method of determining a rotational position of an object in a coordinate system of an associated x-ray imaging device, the method comprising:

providing an x-ray image of an object to which a Moiré marker for x-ray imaging is attached during generation of the x-ray image, the x-ray image having been generated when the object to which the Moiré marker for x-ray imaging is attached is imaged together with the Moiré marker for x-ray imaging by the associated x-ray imaging device, wherein a Moiré pattern of x-ray signal intensities is generated on the x-ray image by the Moiré marker for x-ray imaging when the object to which the Moiré marker for x-ray imaging is attached is imaged together with the Moiré marker for x-ray imaging by the associated x-ray imaging device, wherein the Moiré pattern of x-ray signal intensities generated when the object to which the Moiré marker for x-ray imaging is attached is imaged together with the Moiré marker for x-ray imaging by the associated x-ray imaging device is indicative of an angle between the Moiré marker for x-ray imaging and an x-ray propagation direction of the associated x-ray imaging device in the coordinate system of the associated x-ray imaging device, wherein the object comprises one or more of: a medical robot, a medical instrument, a medical device, a patient support device, and/or a patient, wherein, in the provided x-ray image, the Moiré marker and a further marker are attached to the object as marker array;

determining, based on the Moiré pattern of x-ray signal intensities generated when the object to which the Moiré marker for x-ray imaging is attached is imaged together with the Moiré marker for x-ray imaging by the associated x-ray imaging device, the rotational position of the object in the coordinate system of the associated x-ray imaging device; and automatically identifying the further marker in the provided x-ray image.

9. The method according to claim 8, the method further comprising:

using the automatically identified further marker in the provided x-ray image for calculating a translational position of the Moiré marker within the coordinate system of the x-ray imaging device.

10. The method according to claim 8, wherein the further marker is of an x-ray opaque material and has a ball shape, a cuboid shape, a pyramidal shape, a disc shape, or any combination thereof.

11. A computer-implemented method of determining a rotational position of an object in a coordinate system of an associated x-ray imaging device, the method comprising:

providing an x-ray image of an object to which a Moiré marker for x-ray imaging is attached during generation of the x-ray image, the x-ray image having been generated when the object to which the Moiré marker for x-ray imaging is attached is imaged together with the Moiré marker for x-ray imaging by the associated x-ray imaging device, wherein a Moiré pattern of x-ray signal intensities is generated on the x-ray image by the Moiré marker for x-ray imaging when the object to which the Moiré marker for x-ray imaging is attached is imaged together with the Moiré marker for x-ray imaging by the associated x-ray imaging device, wherein the Moiré pattern of x-ray signal intensities generated when the object to which the Moiré marker for x-ray imaging is attached is imaged together with the Moiré marker for x-ray imaging by the associated x-ray imaging device is indicative of an angle between the Moiré marker for x-ray imaging and an x-ray propagation direction of the associated x-ray imaging device in the coordinate system of the associated x-ray imaging device, wherein the object comprises one or more of: a medical robot, a medical instrument, a medical device, a patient support device, and/or a patient; and determining, based on the Moiré pattern of x-ray signal intensities generated when the object to which the Moiré marker for x-ray imaging is attached is imaged together with the Moiré marker for x-ray imaging by the associated x-ray imaging device, the rotational position of the object in the coordinate system of the associated x-ray imaging device, wherein the determining the rotational position further comprises comparing at least the Moiré pattern of the x-ray signal intensities generated by the Moiré marker in the x-ray image with a target pattern of x-ray intensities to be generated by the Moiré marker.

12. The method according to claim 11, further comprising:

repeating the steps of providing the x-ray image of the object and determining the rotational position of the object, wherein the determining the rotational position of the object comprises comparing at least the Moiré pattern with the target pattern, until a pre-defined match between the generated Moiré pattern in the provided x-ray image and the target pattern is achieved.

13. A Moiré marker for x-ray imaging, the Moiré marker for x-ray imaging comprising:

a layered pattern structure of a plurality of layers comprising at least a first material and a second material, wherein the first material has a higher x-ray opacity than an x-ray opacity of the second material, wherein pattern structures of the first and second materials are configured for generating a Moiré pattern of x-ray signal intensities in an x-ray image when being imaged by an associated x-ray imaging device, wherein the layered pattern structure further comprises:

a first layer with a first pattern of the first material and the second material; and a second layer with a second pattern of the first material and the second material.

14. The Moiré marker for x-ray imaging according to claim 13, wherein the layered pattern structure of the first material and the second material is configured to allow a determination of a rotational position of the Moiré marker for x-ray imaging from the x-ray image of the Moiré marker for x-ray imaging.

15. The Moiré marker for x-ray imaging according to claim 13, wherein the first layer and the second layer are separated from each other by a first distance, wherein the second material of the first pattern and the second material of the second pattern have a first width between two adjacent pattern elements of the first material, and the first distance is larger than the first width.

16. The Moiré marker for x-ray imaging according to claim 13, wherein the first material comprises at least one of lead, tin, bismuth, tungsten, iodine, gold, tantalum, yttrium, niobium, molybdenum, ruthenium, rhodium, barium, lanthanum, cerium, praseodymium, neodymium, samarium, europium, gadolinium, terbium, dysprosium, holmium, erbium, thulium, ytterbium, lutetium, hafnium, rhenium, osmium, iridium, or bismuth, and the second material comprises at least one of air, plastic material, carbon, a composite of a thermoplastic resin with carbon-fiber reinforcement, a thermoplastic polymer, or a combination thereof.

17. A marker array for x-ray imaging, the array comprising:

the Moiré marker for x-ray imaging according to claim 13; and an x-ray marker of an x-ray opaque material having a ball shape, a cuboid shape, a pyramidal shape, a disc shape, or any combination thereof.

18. The Moiré marker for x-ray imaging according to claim 15, wherein the pattern structure comprises:

a third layer with a third pattern of the first material and the second material; and a fourth layer with a fourth pattern of the first material and the second material, wherein the third layer and the fourth layer are separated from each other by a second distance, wherein the second material of the third pattern and the second material of the fourth pattern have a second width between two adjacent pattern elements of the first material, wherein the second distance is larger than the second width, and a ratio of the first width to the first distance is different from a ratio of the second width to the second distance.

* * * * *